US009724188B2

United States Patent
Li et al.

(10) Patent No.: US 9,724,188 B2
(45) Date of Patent: Aug. 8, 2017

(54) SYSTEM AND METHOD FOR LIGAMENT RECONSTRUCTION

(75) Inventors: Guoan Li, Milton, MA (US); Hemanth R. Gadikota, Boston, MA (US); Thomas J. Gill, Weston, MA (US)

(73) Assignee: The General Hospital Corporation, Boston, MA (US)

( * ) Notice: Subject to any disclaimer, the term of this patent is extended or adjusted under 35 U.S.C. 154(b) by 488 days.

(21) Appl. No.: 13/281,557

(22) Filed: Oct. 26, 2011

(65) Prior Publication Data

US 2012/0109299 A1   May 3, 2012

Related U.S. Application Data

(60) Provisional application No. 61/407,296, filed on Oct. 27, 2010.

(51) Int. Cl.
*A61F 2/08* (2006.01)

(52) U.S. Cl.
CPC .............. *A61F 2/0811* (2013.01); *A61F 2/08* (2013.01)

(58) Field of Classification Search
CPC .. A61F 2002/0829; A61F 2/0811; A61F 2/08; A61F 2002/0835
USPC ............ 623/13.14, 17.15, 17.16; 606/63, 68, 606/86 R, 313
See application file for complete search history.

(56) References Cited

U.S. PATENT DOCUMENTS

| 5,603,716 | A | 2/1997 | Morgan et al. |
| 5,683,394 | A * | 11/1997 | Rinner ..................... 606/86 R |
| 5,785,714 | A | 7/1998 | Morgan et al. |
| 5,961,520 | A | 10/1999 | Beck, Jr. et al. |
| 6,203,572 | B1 | 3/2001 | Johnson et al. |
| 6,235,057 | B1 | 5/2001 | Roger et al. |
| 6,537,319 | B2 | 3/2003 | Whelan |
| 6,562,072 | B1 | 5/2003 | Fuss et al. |
| 6,623,524 | B2 | 9/2003 | Schmieding |

(Continued)

FOREIGN PATENT DOCUMENTS

| WO | 2005069884 A2 | 8/2005 |
| WO | 2010045207 A2 | 4/2010 |

OTHER PUBLICATIONS

U.S. Appl. No. 13/122,845. Non-Final Office Action dated Mar. 15, 2013. pp. 1-30.

(Continued)

*Primary Examiner* — Brian Pellegrino
(74) *Attorney, Agent, or Firm* — Quarles & Brady LLP

(57) ABSTRACT

Systems and methods for ligament reconstruction provides an implant configured to position ligaments in the anatomic positions to thereby to restore the native anatomy and function of the reconstructed area. The implant includes a sheath, a first ledge, a second ledge, a first anchor and a second anchor. The sheath has an exterior surface and an interior surface, wherein the interior surface of the sheath forms a lumen configured to receive a sheath expander. The first ledge and the second are configured to separate the ligaments and acts as an anchor for the sheath in the bone tunnel. The first anchor and the second anchor are configured to engage the ligaments and be expandable outwards away from the lumen to provide fixation in a bone tunnel. When the implant receives the sheath expander, the ligaments can be separated, positioned, and secured in the bone tunnel.

22 Claims, 6 Drawing Sheets

(56) References Cited

U.S. PATENT DOCUMENTS

| | | | |
|---|---|---|---|
| 6,887,271 | B2 | 5/2005 | Justin et al. |
| 6,890,354 | B2 | 5/2005 | Steiner et al. |
| 7,066,956 | B2 | 6/2006 | Schmieding et al. |
| 7,077,863 | B2 | 7/2006 | Schmieding et al. |
| 7,137,996 | B2 | 11/2006 | Steiner et al. |
| 7,141,066 | B2 | 11/2006 | Steiner et al. |
| 7,309,356 | B2 | 12/2007 | Steiner |
| 7,326,247 | B2 | 2/2008 | Schmieding et al. |
| 7,329,281 | B2 | 2/2008 | Hays et al. |
| 7,338,492 | B2 | 3/2008 | Singhatat et al. |
| 7,357,803 | B2 | 4/2008 | Singhatat |
| 7,407,512 | B2 | 8/2008 | Bojarski et al. |
| 8,333,802 | B2 | 12/2012 | Dougherty |
| 8,491,652 | B2 | 7/2013 | Fening et al. |
| 2001/0021875 | A1 | 9/2001 | Enzerink et al. |
| 2002/0007182 | A1 | 1/2002 | Kim |
| 2002/0040241 | A1 | 4/2002 | Jarvinen |
| 2002/0055780 | A1 | 5/2002 | Sklar |
| 2003/0171810 | A1 | 9/2003 | Steiner |
| 2003/0171811 | A1 | 9/2003 | Steiner et al. |
| 2005/0096743 | A1 | 5/2005 | Schmieding et al. |
| 2006/0095130 | A1 | 5/2006 | Caborn et al. |
| 2006/0229722 | A1 | 10/2006 | Bianchi et al. |
| 2007/0239275 | A1 | 10/2007 | Willobee |
| 2008/0051887 | A1 | 2/2008 | Carter et al. |
| 2008/0119929 | A1 | 5/2008 | Schmieding et al. |
| 2010/0049319 | A1 | 2/2010 | Dougherty |
| 2011/0196490 | A1 | 8/2011 | Gadikota et al. |
| 2014/0243978 | A1 | 8/2014 | Beck, Jr. et al. |

OTHER PUBLICATIONS

Aglietti, et al., Long-Term Study of Anterior Cruciate Ligament Reconstruction for Chronic Instability Using the Central One-Third Patellar Tendon and a Lateral Extraarticular Tenodesis, The American Journal of Sports Medicine, 1992, 20(1):38-45.

Bach, et al., Single-Incision Endoscopic Anterior Cruciate Ligament Reconstruction Using Patellar Tendon Autograft, The American Journal of Sports Medicine, 1998, 26(1):30-40.

Caborn, et al., Single Femoral Socket Double-Bundle Anterior Cruciate Ligament Reconstruction Using Tibialis Anterior Tendon: Description of a New Technique, Arthroscopy: The Journal of Arthroscopic and Related Surgery, 2005, 21(10):1273.e1-1273.e8.

Duquin, et al., Current Trends in Anterior Cruciate Ligament Reconstruction, J. Knee Surg., 2009, 22(1):7-12.

Fu, et al., Primary Anatomic Double-Bundle Anterior Cruciate Ligament Reconstruction, A Preliminary 2-Year Prospective Study, The American Journal of Sports Medicine, 2008, 36(7):1263-1274.

Georgoulis, et al., Tibial Rotation is Not Restored After ACL Reconstruction with a Hamstring Graft, Clinical Orthopaedics and Related Research, 2006, 454:89-94.

Gill, et al., Anterior Cruciate Ligament Reconstruction, The Two-Incision Technique, Orthop. Clin. N. Am., 2002, 33 (4):727-735.

Jomha, et al., Long Term Osteoarthritic Changes in Anterior Cruciate Ligament Reconstructed Knees, Clinical Orthopaedics and Related Research, 1999, 358:188-193.

Milano, et al., Comparison Between Different Femoral Fixation Devices for ACL Reconstruction with Doubled Hamstring Tendon Graft: A Biomechanical Analysis, Arthroscopy: The Journal of Arthroscopic and Related Surgery, 2006, 22(6):660-668.

Pinczewski, et al., A Five-Year Comparison of Patellar Tendon Versus Four-Strand Hamstring Tendon Autograft for Arthroscopic Reconstruction of the Anterior Cruciate Ligament, The American Journal of Sports Medicine, 2002, 30(4):523-536.

Ristanis, et al., Follow-up Evaluation 2 Years After ACL Reconstruction with Bone-Patellar Tendon-Bone Graft Shows that Excessive Tibial Rotation Persists, Clin. J. Sport Med., 2006, 16(2):111-116.

Schachter, et al., Soft-Tissue Reconstruction of the Anterior Cruciate Ligament with the AperFix System, Operative Techniques in Sports Medicine, 2009, 17:57-61.

Schachter, et al., Single-Tunnel Double-Bundle Anterior Cruciate Ligament Reconstruction, Techniques in Knee Surgery, 2009, 8(2):110-114.

Seon, et al., Comparison of Single- and Double-Bundle Anterior Cruciate Ligament Reconstructions in Restoration of Knee Kinematics and Anterior Cruciate Ligament Forces, The American Journal of Sports Medicine, 2010, 38 (7):1359-1367.

Yasuda, et al., Anatomic Reconstruction of the Anteromedial and Posterolateral Bundles of the Anterior Cruciate Ligament Using Hamstring Tendon Grafts, Arthroscopy: The Journal of Arthroscopic and Related Surgery, 2004, 20 (10):1015-1025.

Depuy Mitek, Bio-Intrafix, Tibial Soft Tissue Fasteners, Data Sheet, 2007, 1 page.

Cayenne Medical, Inc., AperFix System Removal Technique Guide, 2008, 8 pages.

Cayenne Medical, Inc., The AperFix II System Surgical Technique Guide, A Complete Anatomic Solution, 2011, 6 pages.

* cited by examiner

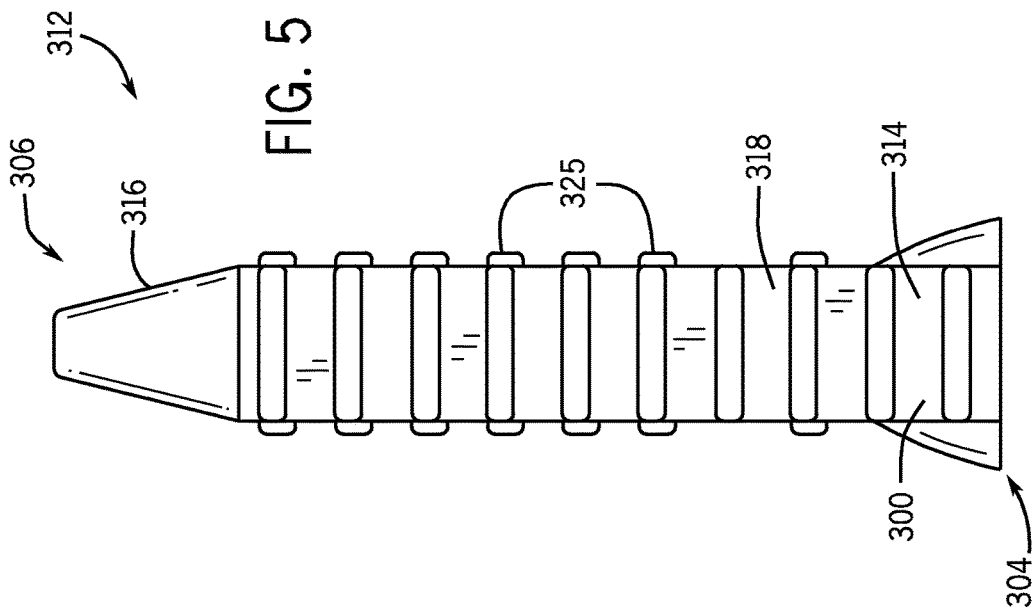
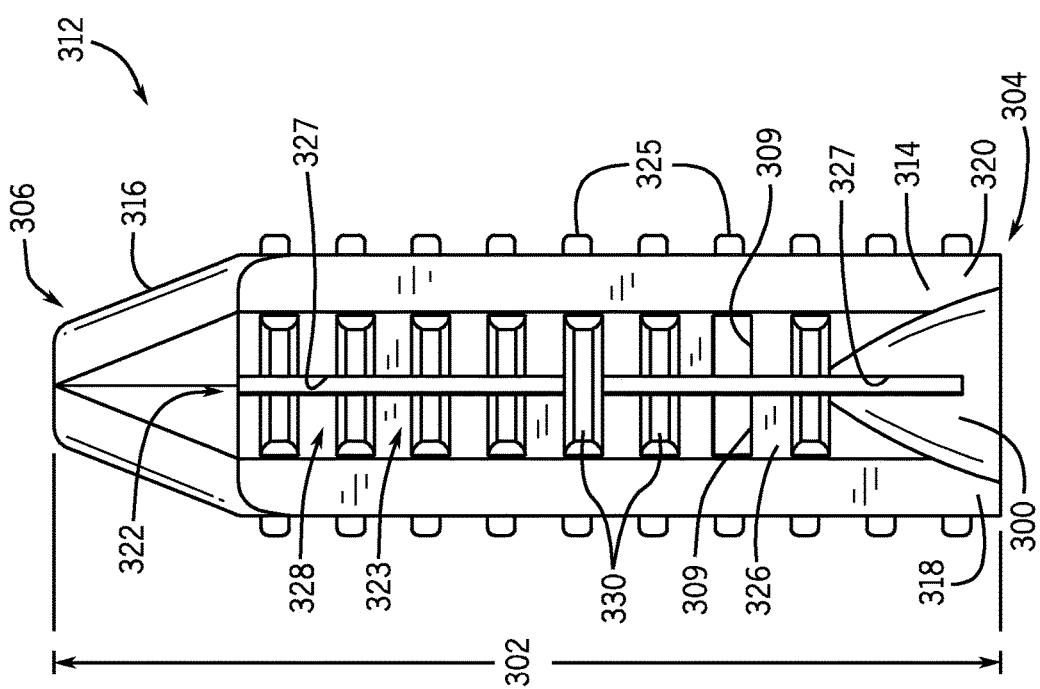

SYSTEM AND METHOD FOR LIGAMENT RECONSTRUCTION

CROSS-REFERENCE TO RELATED APPLICATIONS

This application claims the benefit of U.S. Provisional Patent Application Ser. No. 61/407,296, filed Oct. 27, 2010, and entitled "Single Tunnel, Double Bundle Anterior Cruciate Ligament Reconstruction Using Hamstring Tendon Grafts," which is hereby incorporated by reference.

STATEMENT REGARDING FEDERALLY SPONSORED RESEARCH OR DEVELOPMENT

Not applicable.

FIELD OF THE INVENTION

The present invention generally relates to a system and method for ligament reconstruction in a joint. More particularly, the present invention relates to a method of and an implant for performing a single-tunnel, double-bundle reconstruction in a joint.

BACKGROUND OF THE INVENTION

The anterior cruciate ligament ("ACL") is one of the major ligaments in the knee that connects the thigh bone ("femur") to the shin bone ("tibia"). The ACL is critical to the stability of knee during daily and sports activities. The ACL consists of two functional bundles named for the place where they attach on tibia. Specifically, the two bundles are the anteromedial ("AM") bundle, which inserts more anterior (towards the front) and medial (towards the inside) of tibia, and the posterolateral ("PL") bundle, which inserts most posterior (towards the back) and lateral (towards the outside) of tibia. The AM bundle is the primary restraint to anterior tibial translation throughout the knee flexion. The PL bundle also contributes to the anterior tibial stability at low flexion angles and primarily provides rotational stability to the joint. Although the two bundles have slightly different functions, the bundles do not work independently, but work together to keep the knee stable while still allowing jumping, running, and the like.

There is a high prevalence of ACL injuries both in athletic and non-athletic population. ACL reconstruction is commonly performed to replace an injured ACL. The goal of ACL reconstruction is to restore the native anatomy and function of the ACL. However, osteoarthritis has been reported among patients who had an ACL reconstruction surgery. Improving ACL reconstruction techniques that may restore normal knee stability and prevent joint degeneration remains a subject of continuing debate in sports medicine research.

Currently there are three types of methods and corresponding implants that have been used in ACL reconstruction surgery. The three types are the single-bundle reconstruction, the double-tunnel, double-bundle reconstruction, and the single-tunnel, double-bundle reconstruction.

In a single-bundle reconstruction, the ACL is restored using one graft bundle. Two tunnels (one on tibia and one on femur) are drilled through the knee to house the one graft bundle. One tunnel can be drilled in the center of the attachment of the old ACL on the tibia, right between the AM and PL bundle. The other tunnel can be drilled in the center of the attachment of the old ACL on the femur. Since single-bundle constructions emphasize only on one bundle, typically the AM bundle, it can not recreate the two functional bundles of ACL. Studies have shown that single-bundle ACL reconstruction fails to restore tibial rotation to the intact level. Patients continue to report a feeling of rotational instability and have developed degenerative changes in the knee joint. These observations are attributed to the limitation of using single-bundle ACL reconstruction to reproduce both functional bundles of ACL.

In order to improve on single-bundle ACL reconstruction, especially to provide a better rotational stability, double-tunnel, double-bundle ACL reconstruction was introduced, where ACL is restored using two graft bundles. Compared to single-bundle reconstruction, there are some benefits of a double-bundle reconstruction. Since double-tunnel, double-bundle reconstruction restores both of the AM and PL bundles, it can better restore knee stability compared to single-bundle reconstruction. Nevertheless, double-tunnel, double-bundle reconstruction is a technically challenging procedure. For example, instead of drilling two tunnels for one graft bundle, as in single-bundle reconstruction, double-tunnel, double-bundle reconstruction requires that four tunnels be drilled. The four tunnels include two tibial and two femoral tunnels, for housing two bundles. By drilling two more tunnels, there is an elevated risk of damage to the bone bridge between the two tunnels and an excessive loss of bone. Furthermore, double-tunnel, double-bundle reconstruction is also associated with an increase in the duration of surgery and higher cost compared to the single bundle reconstruction. These limitations in the current designs of the ACL reconstruction techniques leave a large scope for an improvement in the surgery.

To address the deficiency in double-tunnel, double-bundle ACL reconstruction, single-tunnel, double-bundle ACL reconstruction was introduced. Single-tunnel, double-bundle reconstruction uses a single femoral and tibial tunnel and an implant that separates the graft into AM and PL bundles. This reconstruction not only allows the reconstruction of the two functional bundles of the ACL in a single tibial and femoral tunnel to provide superior stability than single-bundle ACL reconstruction, but also is technically less demanding, and decreases operative time. Currently there are two types of implants designed for single-tunnel, double-bundle ACL reconstruction. These implants include the AperFix and Femoral INTRAFIX implants. AperFix is a registered trademark of Cayenne Medical, Inc. of Scottsdale Ariz. INTRAFIX is a registered trademark of Johnson & Johnson of New Brunswick, N.J. There is evidence that neither of these implants can restore normal knee biomechanics.

Therefore, it would be desirable to have an improved system and method for ligament reconstruction, which can better restore the native anatomy and function of the ligament or ligaments in a joint.

SUMMARY OF INVENTION

The present invention overcomes the aforementioned deficiencies by providing a method and implant for single-tunnel, double-bundle reconstruction in a joint. The implant can readily arrange two graft bundles in the anatomic positions of, for example, AM and PL bundles in a single-tunnel, double-bundle ACL reconstruction, thereby to restore the native anatomy and function of the ACL.

In accordance with one aspect of the invention, a surgical implant for implementing a ligament reconstruction in a subject using a first ligament and a second ligament as graft is provided. The implant includes a sheath, a first ledge, a second ledge, a first anchor, and a second anchor. The sheath extends along a length from a first end to a second end to form an exterior surface and an interior surface. The interior surface of the sheath forms a lumen configured to receive a sheath expander. The first ledge and the second ledge are formed on the exterior surface of the sheath and extend along the length of the sheath. The two ledges are formed in a spaced relationship to each other in order to form a first space and a second space extending along the exterior surface of the sheath between the first ledge and the second ledge. The first anchor and the second anchor are formed on the exterior surface of the sheath in the first space and the second space, respectively, and extend along the length of the sheath.

When a first ligament and a second ligament are engaged with an implant in accordance with the present invention and implanted in a bone tunnel of a joint, a first ledge and a second ledge of the implant cause the ligaments to engage with the first anchor and the second anchor, respectively. That is the first ledge and the second ledge of the implant are configured to separate the first ligament and the second ligament and also to penetrate into the bone tunnel to anchor the sheath in it. Furthermore, the first anchor and the second anchor are configured to move from a retracted position to an extended position in response to a sheath expander extending through a lumen formed by a sheath upon which the first and second anchor and the first and second ledge are formed. The first ligament and the second ligament can be readily arranged and secured in a bone tunnel. Therefore, the implant is capable of separating, arranging, and securing the first ligament and the second ligament in the anatomic positions of, for example, AM and PL bundles in a single-tunnel, double-bundle reconstruction.

In accordance with another aspect of the invention, a method for using an implant includes forming a bone tunnel in a joint, such as the knee, to reconstruct the joint, for example, to repair an injured ACL. A K-wire can be inserted through the bone tunnel extending through opposing sides of the joint. A first ligament and a second ligament, along with the implant are passed through the tunnels. The first ligament and the second ligament are rotated in one tunnel until they are positioned. A sheath expander is inserted into the lumen of the implant. The sheath expander firmly engages the first ligament and the second ligament onto the inner surface of the tunnel. After the ligaments are secured in one tunnel, the other end of the ligaments can be oriented in the anatomical bundle footprints, giving rise to the desired bundles. Thereafter, the above-described process for positioning and securing the implant and ligaments is repeated in the other tunnel.

The foregoing and other aspects and advantages of the invention will be made apparent from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 4 is a top view of the implant of FIG. 3.

FIG. 5 is a side view of the implant of FIG. 3.

DETAILED DESCRIPTION

Figure 1:
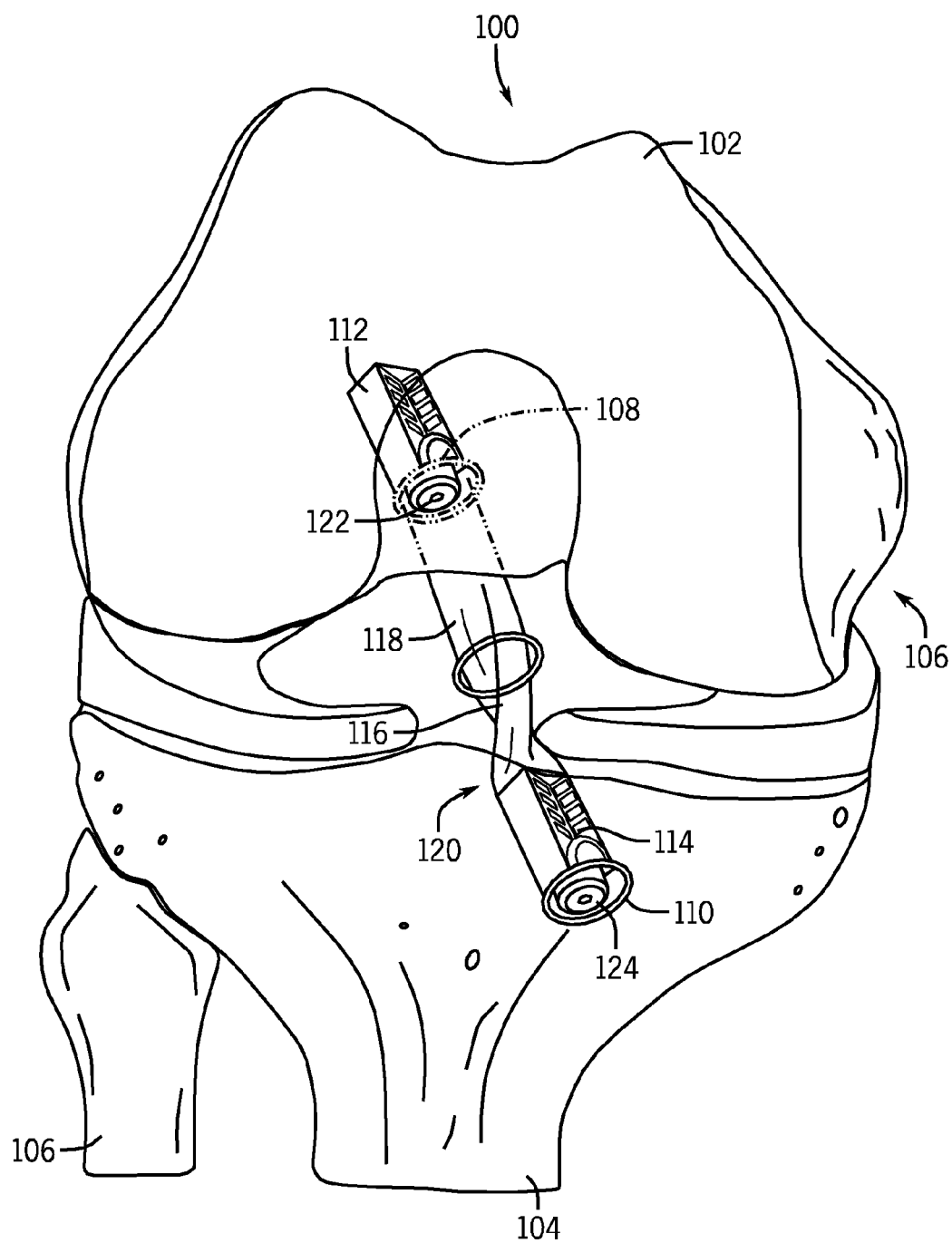
FIG. 1 is a perspective view of a knee joint having an implant utilized in a single-tunnel, double-bundle ACL reconstruction in accordance with embodiments of the present invention.

Referring to FIG. 1, a representative joint 100 is shown. The joint 100 is formed at the meeting of a femur 102, tibia 104, and fibula 106. Formed in the femur 102 is a first, femoral, bone tunnel 108 and formed in the tibia 104 is a second, tibial, bone tunnel 110. Arranged in the bone tunnels 108, 110, are a pair of implants 112, 114 configured for implementing a single-tunnel, double-bundle ACL reconstruction, in accordance with one embodiment of the present invention. Specifically, a first ligament graft 116 and a second ligament graft 118 are formed to be a graft bundle for AM bundle and PL bundle. Hamstring tendon autografts and allografts are preferred graft material used as the first ligament 116 and the second ligament 118. Other graft materials, such as achilles tendon, quadriceps tendon, and tibialis tendon can also be used according to the present invention.

Although FIG. 1 and the description of the invention is given with respect to ACL reconstruction, the present invention can be used for, but not limited to, posterior cruciate ligament ("PCL") and medial collateral ligament ("MCL") reconstruction, and other ligament reconstructions in various joints, such as, but not limited to, shoulder, elbow and ankle joints, for example. ACL reconstruction using the present invention can readily be accomplished by surgeons who are familiar with single bundle reconstruction.

The first implant 112 is engaged with a first end (not shown to allow full view of the first implant 112) of the first ligament 116 and a first end (not shown to allow full view of the first implant 112) of the second ligament 118 into the femoral tunnel 108. The second implant 114 is engaged with a second end 120 of the first ligament 116 and the second ligament 118. As will be described in further detail, the first ligament 116 and the second ligament 118 are separately engaged with the implants 112, 114 in a spaced relationship. As will also be described in further detail, a first sheath expander 122 is engaged with the first implant 112 to secure the first ligament 116 and the second ligament 118 into the femoral tunnel 108. Likewise, a second sheath expander 124 is engaged with the second implant 114 to secure the first ligament 116 and the second ligament 118 into the tibial femoral tunnel 110.

Figure 2:
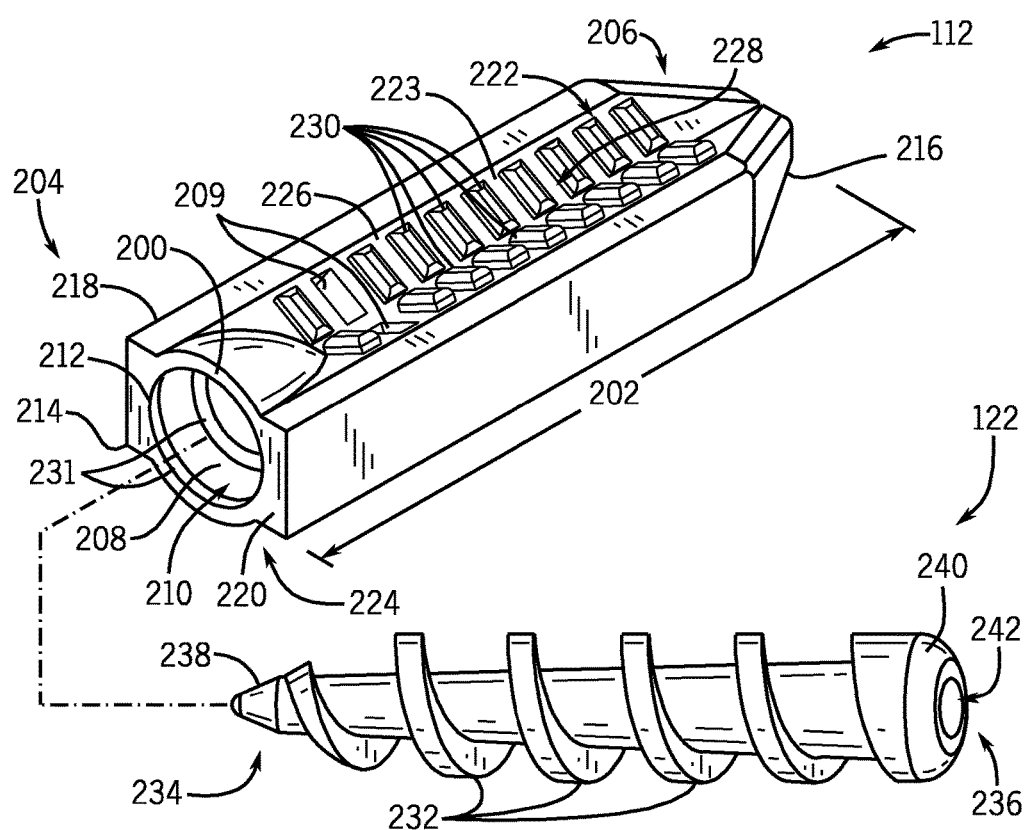
FIG. 2 is a perspective view of the implant of FIG. 1 and a sheath expander for use with the implant, in accordance with embodiments of the present invention.

FIG. 2 shows a perspective view of the implant 112 and the sheath expander 122 as shown in FIG. 1, in accordance with the present invention. Since the first implant 112 and the second implant 114, the first sheath expander 122 and the second sheath expander 124 have substantially identical structure, the implant 112 and the sheath expander 122 are discussed as an example representing both the first implant 112, the second implant 114, the first sheath expander 122 and the second sheath expander 124, respectively.

Referring now to FIG. 2, an implant, for illustrative purposes the first implant 112 of FIG. 1, is shown. It is noted that, for purposes of implementing a single-tunnel, double-bundle reconstruction in accordance with the present invention, the first implant 112 and the second implant 114 of FIG. 1 may be substantially similar. In this case, for purposes of clarity, the description of the implants 112, 114, will focus on the design of the first implant 112.

The implant 112 includes a sheath 200 that extends along a length of the implant 112 illustrated by arrow 202 between a first end 204 and a second end 206. Located at the first end 204 of the sheath is an opening 208 providing access to a lumen 210 formed by an interior surface 212 of the sheath 200 that runs substantially parallel to an exterior surface 214 of the sheath 200. The second end 206 of the sheath 200 may form a taper 216 designed to facilitate insertion into a bone tunnel 108, 110 of FIG. 1.

Formed on the exterior surface 214 of the sheath 200 is a first ledge 218 and a second ledge 220 that extend along the length 202 of the sheath 200. The first ledge 218 and the second ledge 220 are formed in a spaced relationship on the exterior surface 214 of the sheath 200 to form a first space 222 and a second space 224. This planar or flat area 223 formed in the first space 222 and the second space 224 facilitates contact between the ledges 218, 220, ligament grafts 116, 118 and a bone tunnel when arranged in a bone tunnel, thereby, providing strong fixation therein.

In the first space 222, a first anchor 226 is formed on the exterior surface 214 of the sheath 200 and extending along the length 202 of the sheath 200. In the second space 224, though not visible in FIG. 2 is a second anchor that is substantially opposite and substantially similar to the first anchor 226. The first anchor 226 is positioned between the first ledge 218 and the second ledge 220 on a first side of the sheath, and the second anchor is positioned between the first ledge 218 and the second ledge 220 on a second side of the sheath, the first side being 180 degrees about a circumference of the sheath from the second side. The first anchor 226 includes a first furrow 228 and the second anchor includes a second furrow. The furrows 228 form a V-shape extending into the lumen 210. Arranged within the furrow 228 are a plurality of ridges 230. As will be described, the ridges 230 serve to prevent slippage between the ligament grafts 116 and 118 and the implants 112 and 114 and bone tunnels 108 and 110.

The interior surface 212 of the sheath 200 may include threading 231 to facilitate extension of the sheath expander 122 through the lumen 210 when received through the opening 208 of the sheath 200. Accordingly, the sheath expander 122 may include reciprocal threading 232 extending between opposing first and second ends 234, 236. In addition the sheath expander 122 may include a taper 238 arranged at the first end 234 and head 240 formed at the second end 236. In this arrangement, the head 240 may include a socket or other engagement mechanism 242 for accepting a reciprocal driving mechanism.

Figure 3:
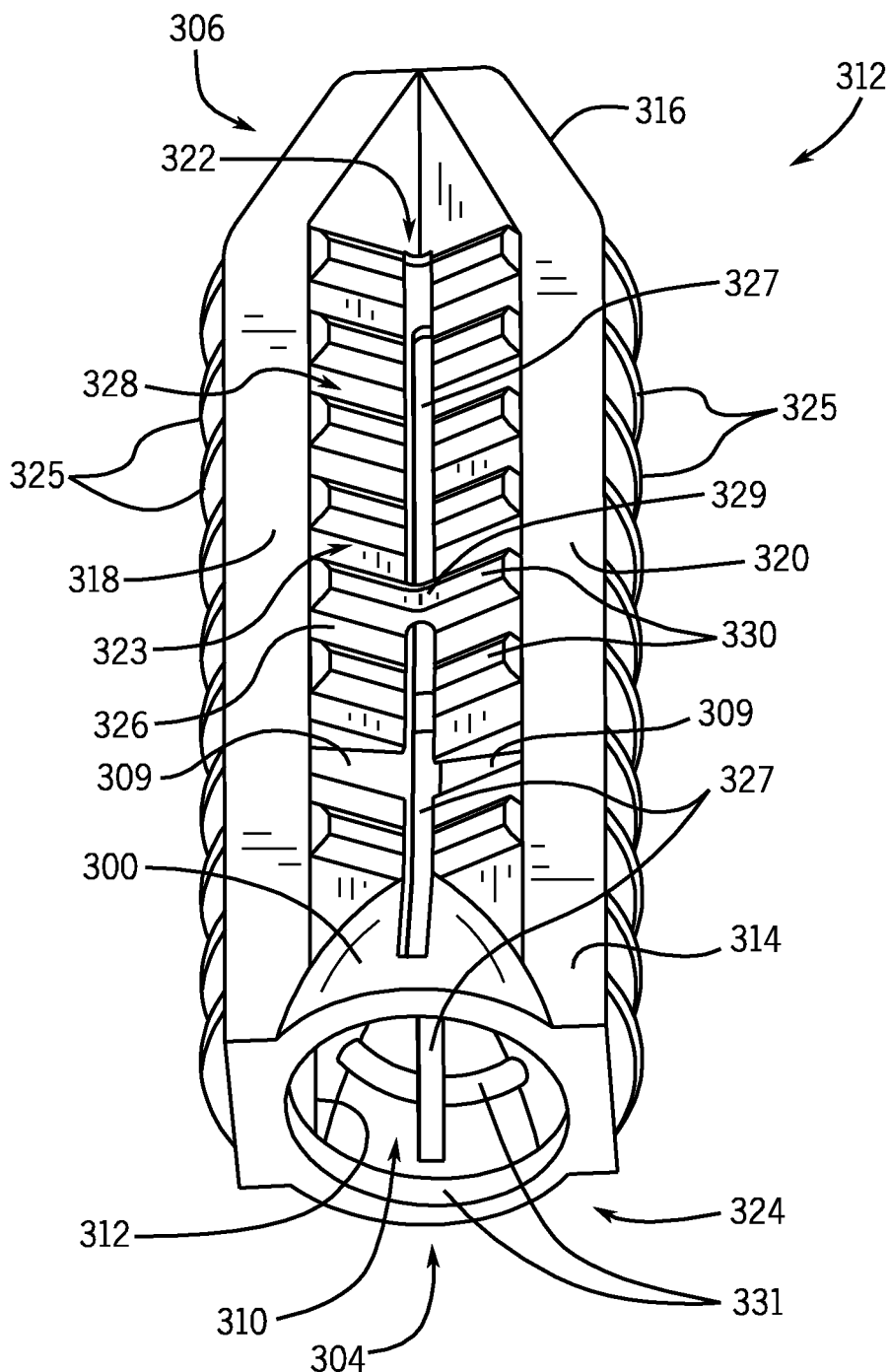
FIG. 3 is a perspective view of an alternative embodiment of the implant of FIG. 1 and a sheath expander for use with the implant, in accordance with embodiments of the present invention.

Referring to FIGS. 3, 4 and 5, an alternative embodiment of the implant 112 is shown. The implant 312 includes a sheath 300 that extends along a length of the implant 312 illustrated by arrow 302 between a first end 304 and a second end 306. Located at the first end 304 of the sheath is an opening 308 providing access to a lumen 310 formed by an interior surface 312 of the sheath 300 that runs substantially parallel to an exterior surface 314 of the sheath 300. The second end 306 of the sheath 300 may form a taper 316 designed to facilitate insertion into a bone tunnel 108, 110 of FIG. 1, for example.

Formed on the exterior surface 314 of the sheath 300 is a first ledge 318 and a second ledge 320 that extend along the length 302 of the sheath 300. The first ledge 318 and the second ledge 320 are formed in a spaced relationship on the exterior surface 314 of the sheath 300 to form a first space 322 and a second space 324 (not visible). A plurality of ribs 325 may be added on one or both ledges 318, 320 of the sheath 300. These ribs 325 may be provided to provide additional contact and prevent the slippage between the sheath 300 and a bone tunnel when arranged in a bone tunnel. The planar or flat area 323 formed in the first space 322 and the second space 324 also facilitates contact between the ledges 318, 320, ligament grafts 116, 118 and a bone tunnel when arranged in a bone tunnel, thereby, providing strong fixation therein.

Longitudinal slots 327 at the vertex of the first space 322 and the second space 324 on one or both sides of the implant may be included. The longitudinal slots may include one or more connection points 329. The longitudinal slots 327 and connection points 329 can facilitate a controlled radial expansion of the sheath 300 when the sheath expander 122 is inserted into the lumen 310, and hence prevent sheath fracture at undesirable locations.

In the first space 322, a first anchor 326 is formed on the exterior surface 314 of the sheath 300 and extending along the length 302 of the sheath 300. In the second space 324, though not visible in FIG. 3, is a second anchor that is substantially opposite and substantially similar to the first anchor 326. The first anchor 326 includes a first furrow 328 and the second anchor includes a second furrow. The furrows 328 form a V-shape extending into the lumen 310. Arranged within the furrow 328 are a plurality of ridges 330. As will be described, the ridges 330 serve to prevent slippage between the ligament grafts 116 and 118 and the implant 312 and a bone tunnel.

The interior surface 312 of the sheath 300 may include threading 331 to facilitate easy insertion and advancement of the sheath expander 122 (see FIG. 2) into and through the lumen 310 when received through the opening 308 of the sheath 300. Accordingly, the sheath expander 122 may include reciprocal threading 232 extending between opposing first and second ends 234, 236. In addition the sheath expander 122 may include a taper 238 arranged at the first end 234 and head 240 formed at the second end 236. In this arrangement, the head 240 may include a socket or other engagement mechanism 242 for accepting a reciprocal driving mechanism. In some embodiments, the first end may include a diameter smaller that the diameter of the second end.

Figure 6A:
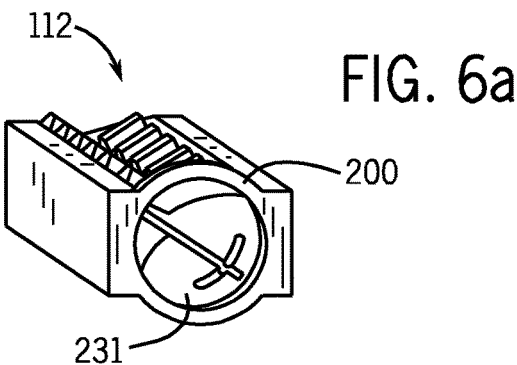
FIGS. 6a-6d are perspective views of the implant of FIG. 1 and sheath expander in various stages of implantation in an associated tunnel, in accordance with embodiments of the present invention.
Figure 6B:
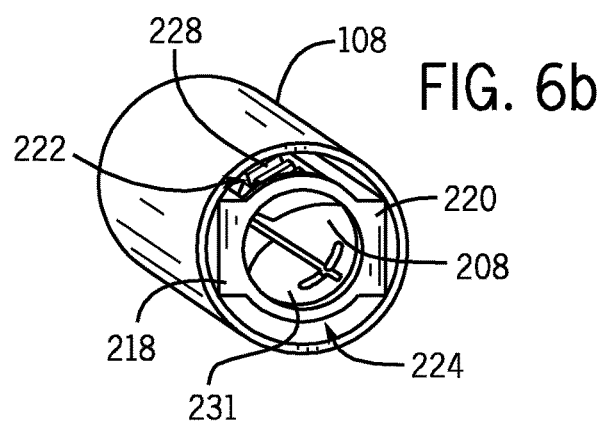

Referring now to FIGS. 6a-6d, the operation and configuration of the implants 112, 114, 312 for performing a single-tunnel, double bundle reconstruction will be described. It is noted that, for purposes of implementing the reconstruction in accordance with the present invention, operation of the implants 112, 114, 312 may be substantially similar. In this case, for purposes of clarity, the description of the operation of implants 112, 114, 312 will focus on the design of the first implant 112. For the purpose of clearly showing the implant 112, the first ligament 116 and the second ligament 118 are ignored in FIG. 6a-6d. As illustrated in FIG. 6a, use of the sheath 200 begins with the sheath 200 being free of additional components. As illustrated in FIGS. 1 and 6b, the implant 112 is arranged in a bone tunnel 108. Again, as described with respect to FIG. 2, the second end 206 of the sheath 200 may include the taper 216 to further facilitate placement. However, as best illustrated in FIG. 6b, the bone tunnel 108 will generally include a diameter sufficient to receive the first and second ledges 218, 220, and ribs 325 in the case of implant 312, that extend along the exterior of the sheath 200 thereby further delineating the first space 222 and second space 224, such that the first and second ligament 116, 118 can be readily arranged in the first space 222 and second space 224, respectively. In this regard, the first and second ligament 116, 118 are separated by the first and second ledges 218, 220 and arranged in the first furrow 228 and the second furrow (obscured in view).

Figure 6C:
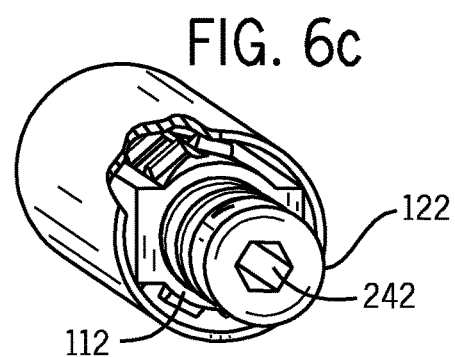

Within this configuration, as best illustrated in FIGS. 2 and 6c, the sheath expander 122 may be extended into the sheath 200. As the sheath expander 122 extends through the opening 208 and into the lumen 210 of the sheath 200, the threading 232 of the sheath expander 122 engages the threading 231 and anchors 226 and associated furrows 228 that, by default are in a retracted position extending into the lumen 210. In this regard, the sheath expander 122 forces the anchors 226 and, particularly, the furrow 228 to extend outward away from the lumen 210 of the sheath 200 into an extended position. That is, the anchors 226 gradually move or deform from a concave form to a convex form extending away from the lumen 210. In this regard, with the furrow 228 extended outward, the anchors 226 thereby serve a plurality of functions. First, the anchors 226 engage the bone tunnel 108 to anchor the sheath 200 in the bone tunnel 108. Second, since the ligaments 116, 118 are arranged in the first and second space 222, 224, respectively, they are likewise engaged by the anchors 226 as they move the furrows 228 into the extended position to lock the ligaments 116, 118 in the first and second space 222, 224, respectively.

Figure 6D:
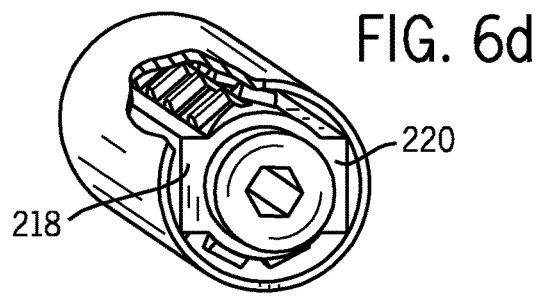

Referring to FIG. 6d, as the sheath expander 122 is fully received by the implant 112, the first anchor 226 and the second anchor are in the extended position. In the extended position, the ridges 230 on the furrow 228 provide desired interference fixation between the first ligament 116 and the tunnel 108, and between the second ligament 118 and the tunnel 108. As a result, this interference fixation can prevent the first ligament 116 and the second ligament 118 from slippage past the sheath 200 and bone. Additionally or alternatively, one or more ridges 230 may be replaced or partially replaced by openings 209, 309 configured to allow the threading 232 of the sheath expander 122 to pass therethrough when engaged with the sheath 200 to thereby engage the ligaments 116, 118 and, in some configurations, even engage the bone tunnel 108. Furthermore, as the sheath expander 122 is inserted into the implant 112, the sheath expander 122 also push the first ledge 218 and the second ledge 220 towards and into the bone tunnel 108. As a result, the first ledge 218 and the second ledge 220, and ribs 325 in the case of implant 312, bite into the bone tunnel 108 and further counter forces that could cause the implant 112 to rotate in the bone tunnel 108 due to torques applied to the implant 112 during engagement with the sheath expander 122. This is at least partially achieved by the opposing configuration of the ledges 218, 220 and the fact that, despite the large spaces 222, 224 that facilitate the placement of substantial bundles, such as used in double-bundle, single-tunnel reconstruction, the design of, for example, only two ledges 218, 220, and ribs 325 in the case of implant 312, arranged in opposition and expanded radially outward away from one another when receiving the sheath expander 122 provides the forces desired to secure the implant in the bone tunnel. It is noted that the implant 112 may continue to be a single continuous piece even after the sheath expander 122 or screw is completely inserted, reducing the risk of relative motion of the two plates formed by the ledges 218, 220. In the case of implant 312, after the sheath expander 122 or screw is completely inserted, the implant remains as a single piece, yet the implant includes the one or more longitudinal slots 327 and connection points 329 to allow for a controlled expansion.

Figure 7:
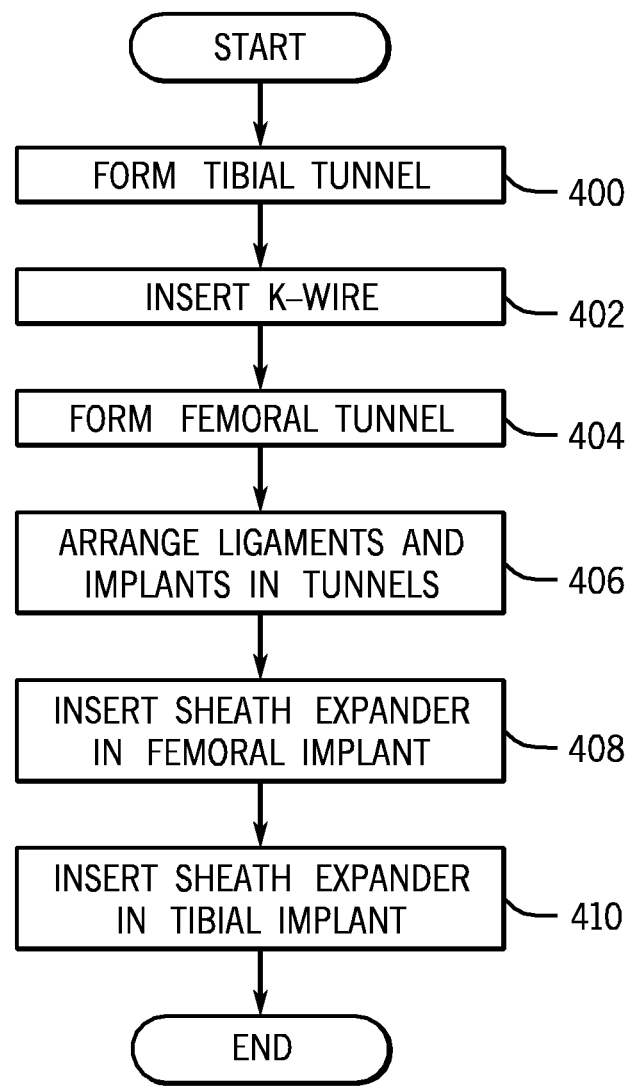
FIG. 7 is a flow chart setting forth the steps of a method of performing an embodiment of a single tunnel, double bundle ACL reconstruction, in accordance with embodiments of the present invention.

This anterior cruciate ligament reconstruction is a minimally invasive surgery that can be performed arthroscopically. Referring to FIG. 7, an exemplary flow chart is provided for a single-tunnel, double-bundle ACL reconstruction using embodiments of the present invention. It is to be appreciated that although described with respect to ACL reconstruction, one of ordinary skill in the art can extend these concepts to other joint/ligament reconstruction.

To perform a reconstruction with the implant, a tibial tunnel can reamed through the anteromedial surface of the tibia at the level of tibial tubercle passing through the landmarks of the center of ACL remnant, as illustrated by process block 400. A K-wire can be inserted through the tibial tunnel aimed at 2 or 10 o'clock position, for example, on the intercondylar clock and 7 mm, or more or less, anterior from the posterior bony edge of the intercondylar wall of the femur, as illustrated by process block 402. At process block 404, a femoral tunnel can be reamed through the tibial tunnel or through a portal independent of the tibial tunnel using a cannulated reamer. The first ligament and the second ligament, along with the implant can be passed through the tibia tunnel or through a portal independent of the tibial tunnel into the femoral tunnel, as represented by process block 406. The first ligament and the second ligament can be rotated in the femoral tunnel until they are positioned in the native AM and PL bundle configuration. At process block 408, a sheath expander can then be inserted clockwise into the lumen of the implant. The sheath expander can firmly engage the first ligament and the second ligament onto the inner surface of the femoral tunnel. After the ligaments are secured at the femoral end, the distal end of the ligaments can be oriented in the anatomical AM and PL bundle footprints, giving rise to the AM and PL bundles. As represented by process block 410, similar to the femoral tunnel, implant and sheath expander can be used to fix the tibial end of the graft.

It is worth noting that the above-described design includes a number of features that are particularly advantageous for facilitating certain surgical procedures. For example, the ledges 218, 220 are advantageously designed to provide large spaces 222, 224 therebetween, while still separating ligaments arranged therebetween and securing the implant. Specifically, the first ledge 218 and the second ledge 220, and ribs 325 in the case of implant 312, bite into the bone tunnel 108 and counter forces that could cause the implant 112 to rotate or move in the bone tunnel 108 due to torques applied to the implant 112 during engagement with the sheath expander 122 or other forces. This is at least partially achieved by the opposing configuration of the ledges 218, 220 and the fact that, despite the large spaces 222, 224 that facilitate the placement of substantial bundles, such as used in double-bundle, single-tunnel reconstruction, the design of, for example, only two ledges 218, 220 arranged in opposition and expanded radially outward away from one another when receiving the sheath expander 122 provides the forces desired to secure the implant in the bone tunnel. Also, by providing substantial spaces 222, 224 and arranging the anchors 226 and associated furrows 228 therein, the anchors 226 are configured to advantageously move between a first position to a second position in response to the sheath expander 122 extending through the lumen of the sheath to thereby engage the anchors 226 with a ligament arranged in the spaces and secure it within the reconstruction. Other configurations with reduced spaces 222, 224 or other such geometries do not achieve the similar ability of the anchors 226 to move between a first position to a second position in response to the sheath expander 122 extending through the lumen and, thus, do not achieve a similar ability to receiving a ligament or ligament bundle, secure the ligament, position/space the ligaments, and protect against movement or undesired forces placed upon the implant.

The detailed description is provided for an implant system and method for using the same in accordance with the present invention. Embodiments are used herein to describe the principles and modes of carrying out the present invention. The above description of embodiments are only to help understand the systems and methods of the present invention. Those skilled in the art may modify modes of carrying out and application scope of the present invention according to the spirit thereof. In summary, the contents of the specification may not be construed as restrictive to the present invention.

What is claimed is:

1. A surgical implant for implementing a ligament reconstruction in a subject using a first ligament and a second ligament, the implant comprising:
    a sheath extending from a first end along a length to a second end to form an exterior surface and an interior surface, wherein the interior surface forms a lumen, the sheath including an end surface between the exterior surface and the interior surface;
    a first ledge formed on the exterior surface of the sheath and extending along the length of the sheath;
    a second ledge formed on the exterior surface of the sheath in a spaced relationship to the first ledge;
    a first anchor formed on the exterior surface of the sheath and extending along the length of the sheath;
    a second anchor formed on the exterior surface of the sheath and extending along the length of the sheath;
    the first anchor positioned between the first ledge and the second ledge on a first side of the sheath, and the second anchor positioned between the first ledge and the second ledge on a second side of the sheath, the first side being 180 degrees about a circumference of the sheath from the second side;
    a sheath expander configured to selectively extend and retract to and from the lumen of the sheath;
    wherein the spaced relationship of the first ledge and the second ledge are configured to cooperate with the sheath to form a barrier separating the first ligament and the second ligament when the implant is implanted in the joint of the subject;
    wherein the first anchor and the second anchor are configured to move between a first position to a second position in response to the sheath expander extending through the lumen of the sheath to thereby engage the first anchor with the first ligament and second anchor with the second ligament, the first position being a concave position and the second position being a convex position; and
    wherein the end surface of the sheath has a perimeter, the perimeter of the end surface of the sheath remains continuous when the sheath expander has been inserted completely into the lumen of the sheath thereby defining an uninterrupted end.

2. The implant of claim 1, wherein the first anchor includes a first furrow and the second anchor includes a second furrow, each of the first and second furrows having formed therein ridges configured to engage the first ligament and the second ligament respectively.

3. The implant of claim 2, wherein, when the first anchor and the second anchor are in the first position, the first furrow and the second furrow are substantially concave to extend into the lumen.

4. The implant of claim 3 wherein when the first anchor and the second anchor are in the first position, the first furrow and the second furrow form a v-shape extending into the lumen.

5. The implant of claim 4 wherein the v-shape extending into the lumen includes a slot at a vertex of the v-shape.

6. The implant of claim 3, wherein, when the first anchor and the second anchor are in the second position, the first furrow and the second furrow are substantially convex to extend away from the lumen.

7. The implant of claim 3, wherein, when the first anchor and the second anchor are in the second position, the ridges of the first furrow and the second furrow are configured to engage the first ligament and the second ligament respectively.

8. The implant of claim 2, wherein the surgical implant is configured for use with the first ligament and the second ligament, first ligament including an anteromedial bundle and the second ligament including a posterolateral bundle.

9. The implant of claim 1, wherein, upon the sheath expander being engaged with the sheath, the first anchor and the second anchor are configured to deform as the sheath expander extends through the lumen to move the first anchor and the second anchor from the first position to the second position.

10. The implant of claim 9, wherein the first position is a retracted position wherein the first anchor and the second anchor extend into the lumen and the second position is an extended position wherein the first anchor and the second anchor extend away from the lumen.

11. The implant of claim 1, further including the sheath expander, the sheath expander extending from a first end having a first diameter to a second end having a second diameter, wherein the first diameter is smaller than the second diameter.

12. The implant of claim 1, wherein the interior of the sheath is configured to receive a plurality of threads formed on the sheath expander to drive the sheath expander through the lumen.

13. The implant of claim 12, wherein the interior of the sheath includes a mating thread to receive at least one of the plurality of threads formed on the sheath expander.

14. The implant of claim 12, wherein the first anchor and the second anchor include at least one opening configured to receive at least one of the plurality of threads formed on the sheath expander as the sheath expander extends through the lumen.

15. The implant of claim 1, wherein the first end of the sheath has a first diameter and the second end of the sheath has a second diameter and wherein the second diameter is smaller than the first diameter.

16. The implant of claim 1, wherein the first anchor and the second anchor are configured to be displaced radially away from the lumen as the sheath expander is extended through the lumen, the sheath being adapted to engage a joint when inserted therein.

17. The implant of claim 1, wherein the surgical implant is for implementing a single-tunnel, double-bundle ligament reconstruction.

18. The implant of claim 1, wherein at least one of the first ledge and the second ledge includes a rib on an outer surface.

19. The implant of claim 1, wherein at least one of the first anchor and the second anchor includes an opening, the opening being configured to receive a thread formed on the sheath expander to drive the sheath expander through the lumen.

20. A surgical implant for implementing a single-tunnel, double-bundle reconstruction in a subject using a first ligament and a second ligament, the implant comprising:
- a sheath extending from a first end along a length to a second end to form an exterior surface and an interior surface, wherein the interior surface forms a lumen, the sheath including an end surface between the exterior surface and the interior surface;
- a first ledge formed on the exterior surface of the sheath and extending along the length of the sheath;
- a second ledge formed on the exterior surface of the sheath in a spaced relationship to the first ledge;
- a first anchor formed on the exterior surface of the sheath and extending along the length of the sheath;
- a second anchor formed on the exterior surface of the sheath and extending along the length of the sheath;
- the first anchor positioned between the first ledge and the second ledge on a first side of the sheath, and the second anchor positioned between the first ledge and the second ledge on a second side of the sheath, the first side being 180 degrees about a circumference of the sheath from the second side;
- a sheath expander configured to selectively extend and retract to and from the lumen of the sheath;
- wherein the first anchor and second anchor are configured to be displaced radially away from the lumen in response to the sheath expander extending through the lumen of the sheath to engage the joint and thereby resist forces applied to the implant to extend the sheath expander through the lumen;
- wherein the spaced relationship of the first ledge and the second ledge are configured to cooperate with the sheath to form a barrier separating the first ligament and the second ligament when the implant is implanted in the joint of the subject;
- wherein the first anchor and the second anchor are configured to move between a first position to a second position in response to the sheath expander extending through the lumen of the sheath to thereby engage the first anchor with the first ligament and second anchor with the second ligament, the first position being a concave position and the second position being a convex position; and
- wherein the end surface of the sheath has a perimeter, the perimeter of the end surface of the sheath remains continuous when the sheath expander has been inserted completely into the lumen of the sheath thereby defining an uninterrupted end.

21. The implant of claim 20, wherein the first anchor includes a first furrow and the second anchor includes a second furrow, each of the first and second furrows having formed therein ridges configured to engage the first ligament and the second ligament respectively.

22. The implant of claim 21, wherein, when the first anchor and the second anchor are in the second position, the first furrow and the second furrow are substantially convex to extend away from the lumen.

* * * * *